(12) United States Patent
Mori et al.

(10) Patent No.: US 7,959,560 B2
(45) Date of Patent: Jun. 14, 2011

(54) BODY INSERTABLE APPARATUS HAVING A PROTECTION CIRCUIT

(75) Inventors: Takeshi Mori, Tokyo (JP); Takemitsu Honda, Tokyo (JP)

(73) Assignee: Olympus Corporation, Tokyo (JP)

( * ) Notice: Subject to any disclaimer, the term of this patent is extended or adjusted under 35 U.S.C. 154(b) by 1101 days.

(21) Appl. No.: 11/632,521

(22) PCT Filed: Jul. 14, 2005

(86) PCT No.: PCT/JP2005/013081
§ 371 (c)(1),
(2), (4) Date: Feb. 12, 2007

(87) PCT Pub. No.: WO2006/006680
PCT Pub. Date: Jan. 19, 2006

(65) Prior Publication Data
US 2007/0265501 A1 Nov. 15, 2007

(30) Foreign Application Priority Data
Jul. 15, 2004 (JP) .................................. 2004-208399

(51) Int. Cl.
*A61B 1/00* (2006.01)
*A61B 1/04* (2006.01)
(52) U.S. Cl. .................... 600/118; 600/117; 320/136
(58) Field of Classification Search .................. 600/117, 600/118, 160; 320/135, 136
See application file for complete search history.

(56) References Cited

U.S. PATENT DOCUMENTS

| 5,604,531 A | 2/1997 | Iddan et al. |
| 6,951,536 B2 * | 10/2005 | Yokoi et al. ................. 600/128 |
| 7,615,006 B2 * | 11/2009 | Abe .............................. 600/118 |
| 2003/0060734 A1 | 3/2003 | Yokoi et al. |
| 2004/0004464 A1 | 1/2004 | Tsukamoto et al. |
| 2004/0087832 A1 | 5/2004 | Glukhovsky et al. |

FOREIGN PATENT DOCUMENTS

| JP | 2001-212080 | 8/2001 |
| JP | 2002-345743 | 12/2002 |
| JP | 2003-325440 | 11/2003 |
| JP | 2004-148124 | 5/2004 |
| WO | WO 01/35813 A1 | 5/2001 |

* cited by examiner

*Primary Examiner* — John P Leubecker
(74) *Attorney, Agent, or Firm* — Scully, Scott, Murphy & Presser, P.C.

(57) ABSTRACT

A protection circuit 26c detects a voltage at a point A on an electric-power supply path from a battery 29 to an intra-capsule function executing circuit 30. When the voltage at the point A becomes smaller than a predetermined threshold value (a predetermined midpoint potential), the protection circuit 26c performs a switching control of a switch element 26a, connects the battery 29 to a resistive load 26b, stops supplying driving power to the intra-capsule function executing circuit 30 and at the same time enables to supply electric power to the resistive load 26b, and prevents a false operation of a circuit at the midpoint potential by exhausting the electric power stored in the battery 29 by the resistive load 26b.

4 Claims, 6 Drawing Sheets

US 7,959,560 B2

BODY INSERTABLE APPARATUS HAVING A PROTECTION CIRCUIT

TECHNICAL FIELD

The present invention relates to a body insertable apparatus that supplies electric power to each of units in, for example, a swallowable capsule endoscope, and specifically to a body insertable apparatus that implements electric power exhaustion of a battery.

BACKGROUND ART

Recently, a capsule endoscope including an imaging function and a radio communication function has been proposed in the filed of an endoscope. The capsule endoscope is configured to be swallowed by an examinee as a subject for an observation (examination) to travel inside organs (inside of a body cavity) such as a stomach or a small intestine by a peristaltic movement to capture images one by one by using the imaging function, during an observation period until the capsule endoscope is naturally excreted from a body of the examinee (human body).

During the observation period in which the capsule endoscope travels inside the organs, image data captured inside the body cavity by the capsule endoscope is sequentially transmitted to an external device provided outside the subject, through the radio function such as a radio communication, and stored in a memory provided in the external device. By carrying the external device including the radio function and a memory function, the examinee can move without inconvenience during the observation period from when the examinee swallows the capsule endoscope until the capsule endoscope is excreted. After the observation is finished, a doctor or a nurse can make a diagnosis by displaying body cavity images on a display unit such as a display, based on the image data stored in the memory of the external device.

The above type of the capsule endoscope includes such a swallowable type as disclosed in Patent Document 1, and such a configuration has been proposed that the capsule endoscope internally includes a reed switch that switches ON/OFF by an external magnetic field for controlling a drive of the capsule endoscope, and is accommodated in a package that includes a permanent magnet for providing the external magnetic field. In other words, the reed switch provided in the capsule endoscope has a configuration to keep an OFF state under such a circumstance that a magnetic field having larger strength than a predetermined strength is provided, and to switch to an ON state as the strength of the external magnetic field decreases. Accordingly, when accommodated in the package, the capsule endoscope is not activated. By removing the capsule endoscope from the package when the capsule endoscope is swallowed, the capsule endoscope is moved away from the permanent magnet to be unaffected from the magnetic strength, and starts to drive. With the above configuration, when accommodated in the package, the capsule endoscope is not to be activated, and after being removed from the package, the capsule endoscope captures an image by an illuminating function and the imaging function and transmits an image signal by the radio function.

Patent Document 1: International application No. 01/35813 pamphlet

Patent Document 2: Japanese Patent Application Laid-Open No. 2002-345743

DISCLOSURE OF INVENTION

Problem to be Solved by the Invention

However, because the capsule endoscope drives a function executing unit that performs a previously set predetermined function such as the illuminating function, the imaging function, and the radio function by supplying electric power from a battery such as a button-type dry battery, if the battery is used for a long time, supply capability of the battery is lowered to be at a midpoint potential. Due to the midpoint potential, a latch-up phenomenon is generated to a load side of the function executing unit and the function executing unit is to be in a failure mode. In response to the above, it can be considered to have a circuit configuration in which the battery and the function executing unit are disconnected at the midpoint potential. However, even with the above configuration, there still is a problem that an operation of a switching circuit for performing a disconnection becomes unstable, the latch-up phenomenon is generated, and therefore, a false operation of the circuit is generated. Further, as disclosed in Patent Document 2, the battery can be used with low power consumption; however, the above problems cannot be solved in such a situation that the battery is used for a long time.

The present invention is made in view of the above problems and an object of the present invention is to provide a body insertable apparatus that enables to prevent a false operation of a circuit at a midpoint potential, by exhausting the electric power stored in a battery in the body insertable apparatus.

Means for Solving Problem

A body insertable apparatus according to the present invention includes a function executing unit that executes a predetermined function in a body into which the body insertable apparatus is inserted; an electric-power accumulating unit that accumulates driving power for driving the function executing unit; a detector that detects electric power supplied from the electric-power accumulating unit; an exhaustion unit that is provided separately from the function executing unit and exhausts the electric power in the electric-power accumulating unit; and a switching controller that switches electric power supply from the electric-power accumulating unit, from the function executing unit to the exhaustion unit, based on a detection result of the detector.

In the body insertable apparatus according to the invention, the switching controller may switch the electric power supply from the function executing unit to the exhaustion unit at one time, based on the detection result of the detector.

In the body insertable apparatus according to the invention, the switching controller may supply electric power from the electric-power accumulating unit to the function executing unit and to the exhaustion unit at the same time, and subsequently may perform a switching for making the electric power supply to the function executing unit terminatably, based on the detection result of the detector.

In the body insertable apparatus according to the invention, the function executing unit may comprise: an illuminating unit that illuminates an inside of the body; an acquiring unit that acquires image information on the illuminated inside of the body; and a radio transmitting unit that wirelessly transmits the image information on the inside of the body acquired by the acquiring unit to an outside, and the switching controller may switch the electric power supply from the electric-power accumulating unit to the function executing unit and to the exhaustion unit, based on the detection result of the detector and a predetermined error rate of the image information.

Effect of the Invention

The body insertable apparatus according to the present invention enables to prevent a false operation of a circuit at a midpoint potential, by exhausting electric power stored in a battery in the body insertable apparatus by switching electric power supply from an electric-power accumulating unit, from a function executing unit to an exhaustion unit, at one time or in stages, based on a detection result by a detector.

EXPLANATIONS OF LETTERS OR NUMERALS

Figure 1:
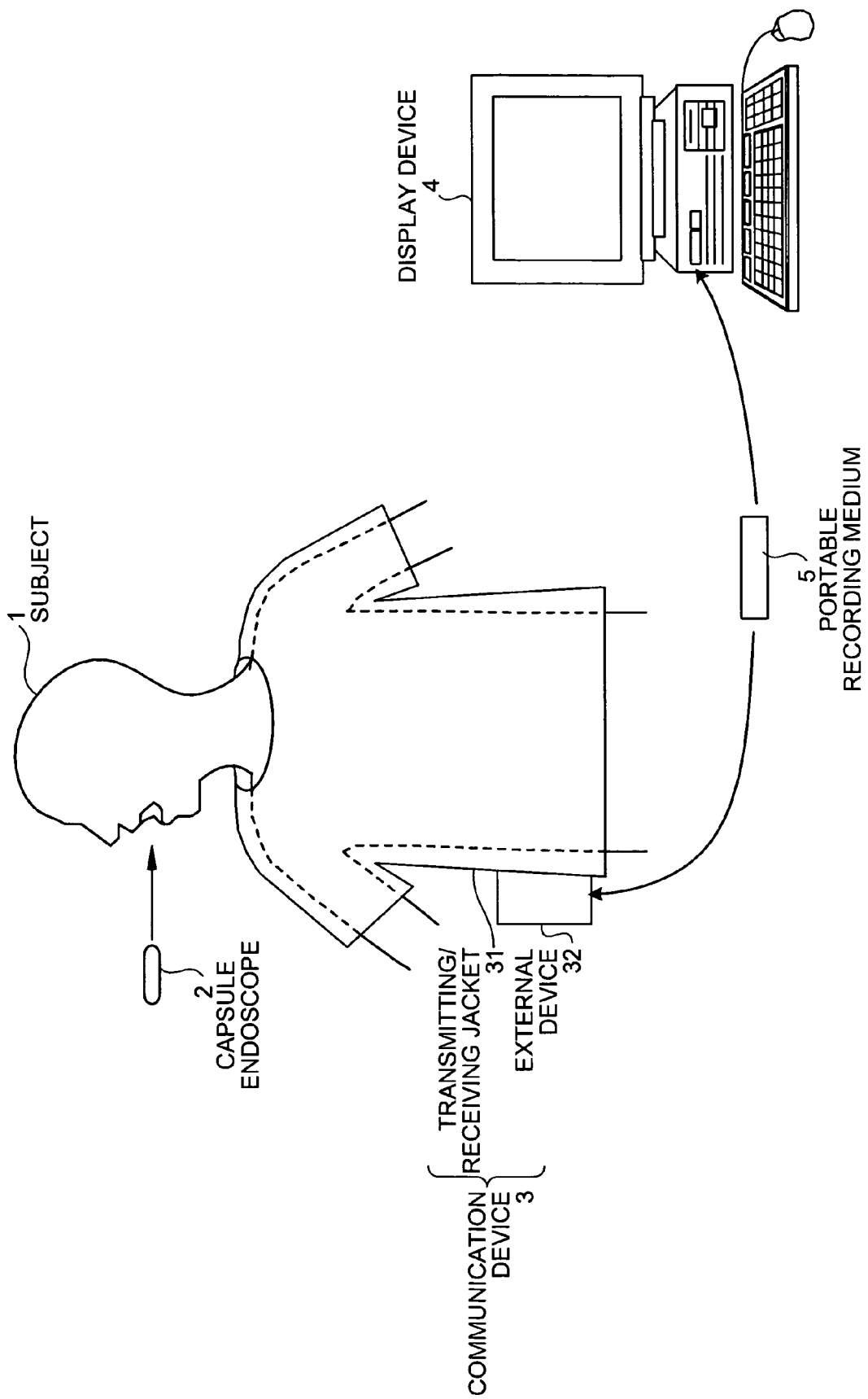
FIG. 1 is a system schematic view for describing a concept of a wireless in-vivo information acquiring system according to an embodiment of the present invention.

1 Subject
2 Capsule endoscope
3 Communication device
4 Display device
5 Portable recording medium
20 Light emitting diode (LED)
21 LED driving circuit
22 Charge coupled device (CCD)
23 CCD driving circuit
24 RF transmitting unit
25 Transmitting antenna unit
26 System control circuit
26a Switch element
26b Resistive load
26c Protection circuit
26d Field effect transistor (FET)
26e Voltage detecting circuit
27 Receiving antenna unit
28 Control-signal detecting circuit
29 Battery
30 Intra-capsule function executing circuit
31 Transmitting/receiving jacket
32 External device
33 RF receiving unit
34 Image processing unit
35 Storage unit
36 Control-signal input unit
37 RF-transmitting unit circuit
38 Power supply unit
A1 to An Receiving antenna
B1 to Bm Transmitting antenna

BEST MODE(S) FOR CARRYING OUT THE INVENTION

Exemplary embodiments of a body insertable apparatus are described below in detail with reference to the accompanying drawings FIG. 1 to FIG. 8. In the below drawings, same components shown in FIG. 1 are assigned with same reference numerals for a convenience of the description. The present invention is not limited to the below embodiments and various modifications can be made without departing from the spirit or scope of the present invention.

First Embodiment

FIG. 1 is a system schematic view for describing a concept of a wireless in-vivo information acquiring system according to the present invention. In FIG. 1, the wireless in-vivo information acquiring system includes a swallowable capsule endoscope 2 as the body insertable apparatus to be inserted into a body cavity of a subject 1, and a communication device 3 that is an extracorporeal device provided outside the subject 1 for wirelessly communicating various types of information with the capsule endoscope 2. The wireless in-vivo information acquiring system includes a display device 4 that displays an image based on data received by the communication device 3, and a portable recording medium 5 that inputs and outputs data between the communication device 3 and the display device 4.

Figure 2:
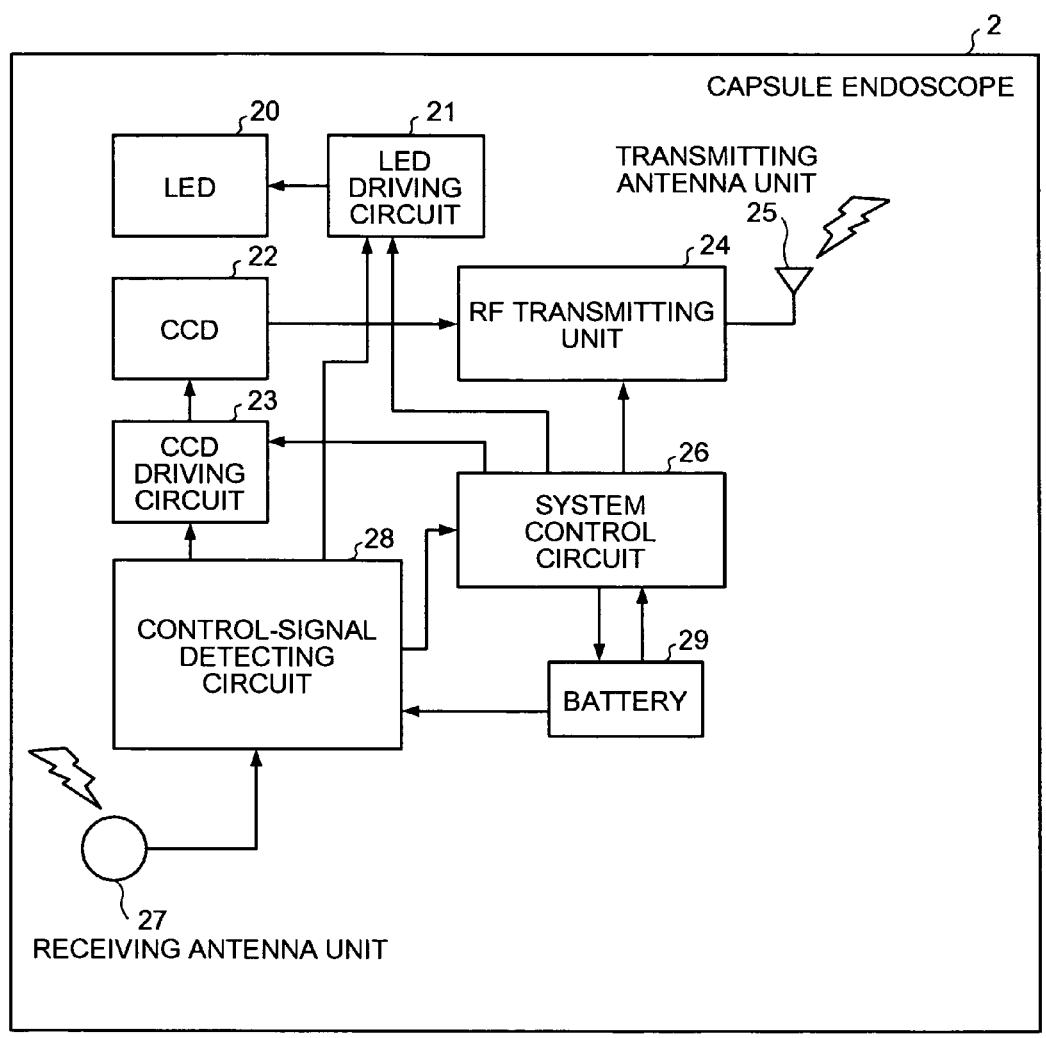
FIG. 2 is a block diagram of an internal configuration of a capsule endoscope shown in FIG. 1.

The capsule endoscope 2, as shown in a block diagram of FIG. 2, includes a light emitting diode (LED) 20 as an illuminating unit for illuminating an examined region in the body cavity of the subject 1, an LED driving circuit 21 as a driving unit for controlling a drive state of the LED 20, a charge coupled device (CCD) 22 as an acquiring unit for capturing a body cavity image (in-vivo information) that is a reflected light from a region illuminated by the LED 20, a CCD driving circuit 23 as a first driving unit for controlling a drive state of the CCD 22, a radio frequency (RF) transmitting unit 24 that modulates a captured image signal into an RF signal, and a transmitting antenna unit 25 as a radio transmitting unit for wirelessly transmitting the RF signal output from the RF transmitting unit 24. Further, the capsule endoscope 2 includes a system control circuit 26 that controls an operation of the LED driving circuit 21, the CCD driving circuit 23, and the RF transmitting unit 24, and performs so that the image data of the examined region illuminated by the LED 20 is acquired by using the CCD 22 while the capsule endoscope 2 is inserted in the subject 1. The acquired image data is converted into the RF signal by the RF transmitting unit 24 and transmitted to the outside of the subject 1 via the transmitting antenna unit 25.

The capsule endoscope 2 further includes a receiving antenna unit 27 as a radio receiving unit that is configured to enable to receive a radio signal transmitted from the communication device 3, a control-signal detecting circuit 28 that detects a control signal of a predetermined input level (i.e., reception strength level) from a signal received by the receiving antenna unit 27, and a battery 29 that supplies electric power to the system control circuit 26 and the control-signal detecting circuit 28.

The control-signal detecting circuit 28 detects contents of the control signal and outputs the control signal to the LED driving circuit 21, the CCD driving circuit 23, and the system control circuit 26, if required. The system control circuit 26 includes a function for distributing a driving power supplied from the battery 29 to other components (function executing units). According to the present embodiment, components including an imaging function, an illuminating function, and a radio function (a part) installed in the capsule endoscope 2 are collectively named as the function executing unit that executes predetermined functions. More specifically, components other than the system control circuit 26, the receiving antenna unit 27, and the control-signal detecting circuit 28 are the function executing units that execute the predetermined functions, and collectively named as an intra-capsule function executing circuit 30 if necessary in this document.

Figure 3:
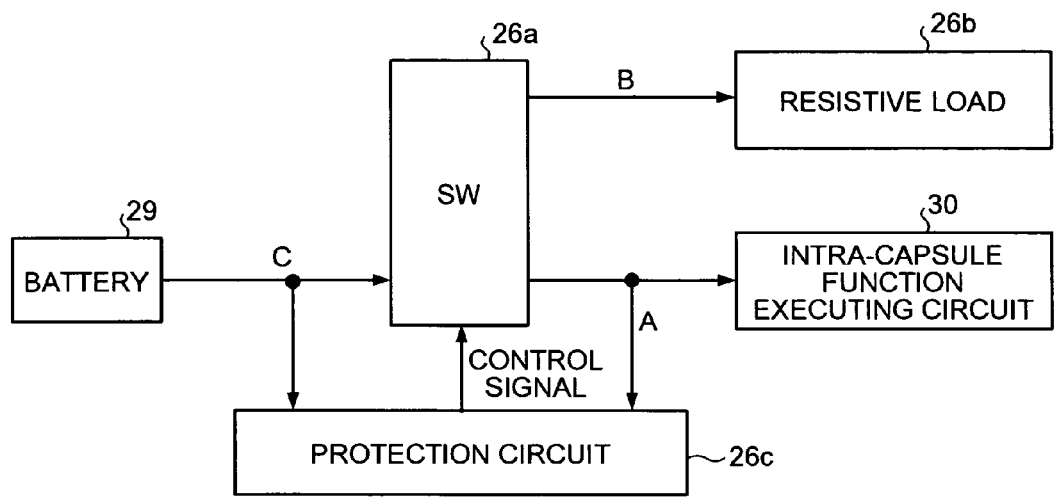
FIG. 3 is a block diagram of a circuit configuration of a system control circuit shown in FIG. 2, according to a first embodiment of the present invention.

FIG. 3 is a circuit diagram for describing a circuit configuration of a system control circuit shown in FIG. 2, according to the first embodiment. In FIG. 3, the battery 29 is configured by, for example, a plurality of button-type dry batteries as a power supply unit.

Figure 4:
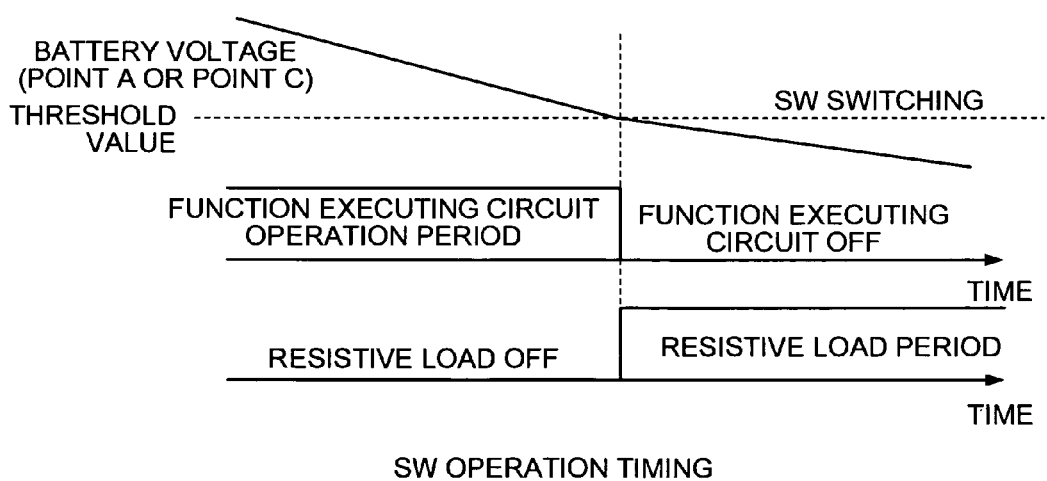
FIG. 4 is a schematic view for describing a threshold value set in a protection circuit shown in FIG. 3 and a switching timing of a switch element based on the threshold value.

The system control circuit 26 includes a resistive load 26b as an exhaustion unit, a switch element 26a for performing a connection switching between the battery 29 and the intra-capsule function executing circuit 30 or between the battery 29 and the resistive load 26b, and a protection circuit 26c that performs a switching control of the switch element 26a. The switch element 26a supplies driving power from the battery 29 to the intra-capsule function executing circuit 30 and, as shown in FIG. 4, the intra-capsule function executing circuit 30 is to be in an operation period while the resistive load 26b is to be in an OFF state. The protection circuit 26c includes a function as a detector for detecting electric power supplied from the battery 29, and a function as a switching controller for performing the switching control of the switch element 26a based on the detected electric power.

In other words, the protection circuit 26c is supplied with the driving power at a point C on the side of the battery 29, while the protection circuit 26c detects a voltage value at a point A on the side of the intra-capsule function executing circuit 30. In the protection circuit 26c, a threshold value is set in advance at a predetermined midpoint potential. As shown in FIG. 4, the threshold value is set in advance as a value with which, when the voltage value at the point A becomes smaller than the midpoint potential, performing a normal operation of the intra-capsule function executing circuit 30 becomes difficult, while an operation of the protection circuit 26c is less affected. When the detected voltage value becomes smaller than the predetermined threshold value, the protection circuit 26c determines that the normal operation of the intra-capsule function executing circuit 30 is interrupted, and outputs the control signal for a switching to the switch element 26a. When the control signal is input, the switch element 26a switches a connection from a side of the intra-capsule function executing circuit 30 to a side of the resistive load 26b to connect the battery 29 to the resistive load 26b and to terminate the electric power supply to the intra-capsule function executing circuit 30, and at the same time, a period for supplying the electric power stored in the battery 29 to the resistive load 26b is initiated and the switch element 26a causes the resistive load 26b to exhaust the stored electric power.

Figure 5:
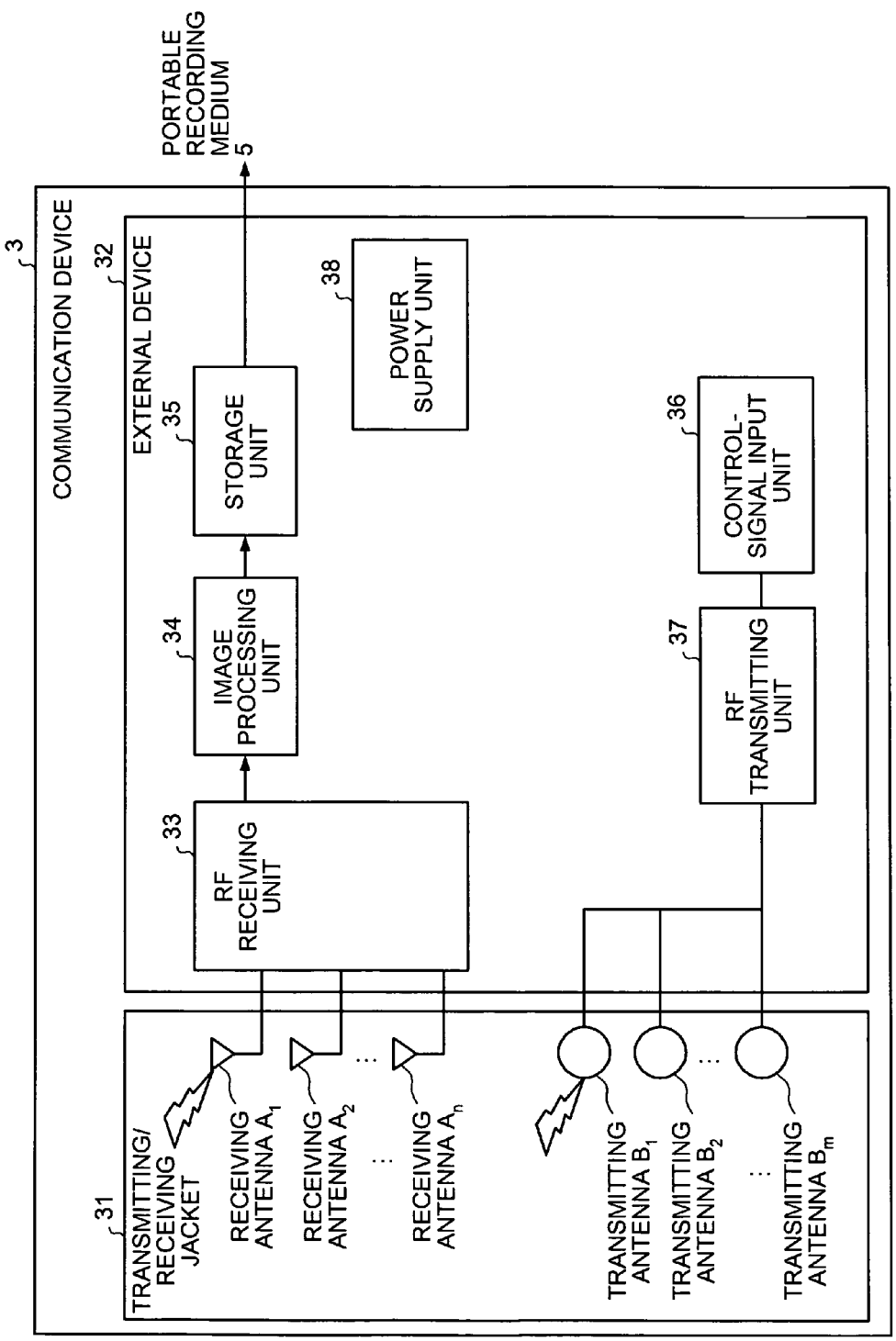
FIG. 5 is a block diagram of an internal configuration of a communication device shown in FIG. 1.

The communication device 3 includes functions of a transmitting device as the radio transmitting unit for transmitting a boot signal to the capsule endoscope 2, and of a receiving device as the radio receiving unit for receiving the image data of the inside of the body cavity transmitted by radio from the capsule endoscope 2. FIG. 5 is a block diagram for describing an internal configuration of the communication device 3 shown in FIG. 1. In FIG. 5, the communication device 3 includes a transmitting/receiving cloths (i.e., a transmitting/receiving jacket) 31 that is to be worn by the subject 1 and includes a plurality of receiving antennas A1 to An and a plurality of transmitting antennas B1 to Bm, and an external device 32 that performs a signal process for the transmitted and received radio signal. At this state, n and m represent arbitral numbers of the antennas set on request basis.

The external device 32 includes an RF receiving unit 33 that performs such a predetermined signal process as a demodulation for the radio signal received by the receiving antennas A1 to An, and that extracts, from the radio signal, the image data acquired by the capsule endoscope, an image processing unit 34 that performs a necessary image process for the extracted image data, and a storage unit 35 for storing the image data for which the image process has been performed, and performs a signal process of the radio signal transmitted by the capsule endoscope 2. According to the present embodiment, the image data is recorded in the portable recording medium 5 via the storage unit 35.

The external device 32 further includes a control-signal input unit 36 that generates a control signal (boot signal) for controlling a drive state of the capsule endoscope 2, and an RF-transmitting unit circuit 37 that converts the generated control signal into a wireless frequency and outputs the signal. The signal converted by the RF-transmitting unit circuit 37 is output to the transmitting antennas B1 to Bm and transmitted to the capsule endoscope 2. The external device 32 further includes a power supply unit 38 that includes a predetermined electric storage device or an alternating-current (AC) power adaptor, and each of components in the external device 32 uses electric power supplied from the power supply unit 38, as driving energy.

The display device 4 is for displaying the body cavity image captured by the capsule endoscope 2, and has a configuration of, for example, a workstation that performs an image display based on the data obtained by the portable recording medium 5. More specifically, the display device 4 can be configured to directly display the image by a cathode-lay tube (CRT) display or a liquid crystal display, or to output the image to other media such as a printer.

The portable recording medium 5 is connectable to the external device 32 and the display device 4, and includes a configuration that enables to output and record information when the portable recording medium 5 is inserted and connected to the both devices. According to the present embodiment, the portable recording medium 5 is inserted into the external device 32 and records data transmitted from the capsule endoscope 2 while the capsule endoscope 2 travels inside the body cavity of the subject 1. Thereafter, the configuration is such that, when the capsule endoscope 2 is excreted from the subject 1, that is, when an imaging of the inside of the subject 1 is finished, the portable recording medium 5 is removed from the external device 32 and inserted into the display device 4, and the recorded data is read out onto the display device 4 by the display device 4. For example, the portable recording medium 5 is configured by, i.e., a compact flash (registered trademark) memory, and a data input and a data output between the external device 32 and the display device 4 can be indirectly performed via the portable recording medium 5. As a result, the subject 1 can freely move while the body cavity image is captured, unlike such a case that the external device 32 and the display device 4 are directly connected with a wire.

Next, an operation of the capsule endoscope 2 according to the first embodiment is described with a block diagram of FIG. 3. In FIG. 3, for example, the capsule endoscope 2 that is still not inserted into the subject 1 accommodates a not shown reed switch that switches ON/OFF by an external magnetic field and is stored in such a state as being installed in a package that includes a permanent magnet for providing the external magnetic field. At this state, the capsule endoscope is not activated. If the capsule endoscope is removed from the package when swallowed, the capsule endoscope is moved away from the permanent magnet and to be unaffected from the magnetic strength, and the electric power is supplied from the battery 29 to the protection circuit 26c. Due to the electric power supply, the protection circuit 26c drives to connect the switch element 26a to the side of the intra-capsule function executing circuit 30, and therefore, the driving energy is supplied from the battery 29 to the intra-capsule function executing circuit 30.

The protection circuit 26c detects the voltage at the point A, and when the voltage value is not smaller than the set threshold value, the protection circuit 26c determines that the intra-capsule function executing circuit 30 is capable of performing a normal operation, and keeps a state of the switch element 26a connected to the side of the intra-capsule function executing circuit 30. Alternately, when the voltage value detected at the point A becomes smaller than the threshold value, the protection circuit 26c determines that the intra-capsule function executing circuit 30 is incapable of performing a normal operation, and connects the switch element 26a to the side of the resistive load 26b. Therefore, the electric power stored in the battery 29 can be exhausted by the resistive load 26b, with an inclination characteristic as shown in FIG. 4.

As described, according to the present embodiment, when the battery voltage becomes smaller than the predetermined threshold value (midpoint potential), a switching from the intra-capsule function executing circuit 30 to the resistive load 26b is performed, and a termination of the electric power supply to the intra-capsule function executing circuit 30 and an exhaustion of the electric power stored in the battery 29 are simultaneously performed. As a result, the electric power stored in the battery in the body insertable apparatus can be exhausted, and a false operation of a circuit at the midpoint potential can be prevented.

Although the voltage value at the point A is detected according to the present embodiment, it is acceptable to detect the voltage value at the point C, and it is acceptable to configure so that, for the battery voltage to be detected, for example, the variation amount of the voltage in a predetermined time period is detected and the switching of the switch element 26a is performed when the variation amount becomes not smaller than the threshold value.

When a consumption of the electric power supplied to the intra-capsule function executing circuit proceeds, the RF-transmitting unit circuit 37 becomes unable to function properly, a transmission error for a transmission of the image data occurs, and the transmission of the image data cannot properly be performed. As described, there is a correlation between a transmission error rate and the battery voltage to be consumed. Accordingly, such a configuration can be acceptable that the battery voltage corresponding to the error rate of the image data within an allowable range is set as the threshold value, and the switching of the electric power supply from the battery to the intra-capsule function executing circuit and to the resistive load is performed based on the detected battery voltage and the threshold value. In this case, it is possible to improve a reliability of the image data, in addition to achieve the above described effect.

Second Embodiment

Figure 6:
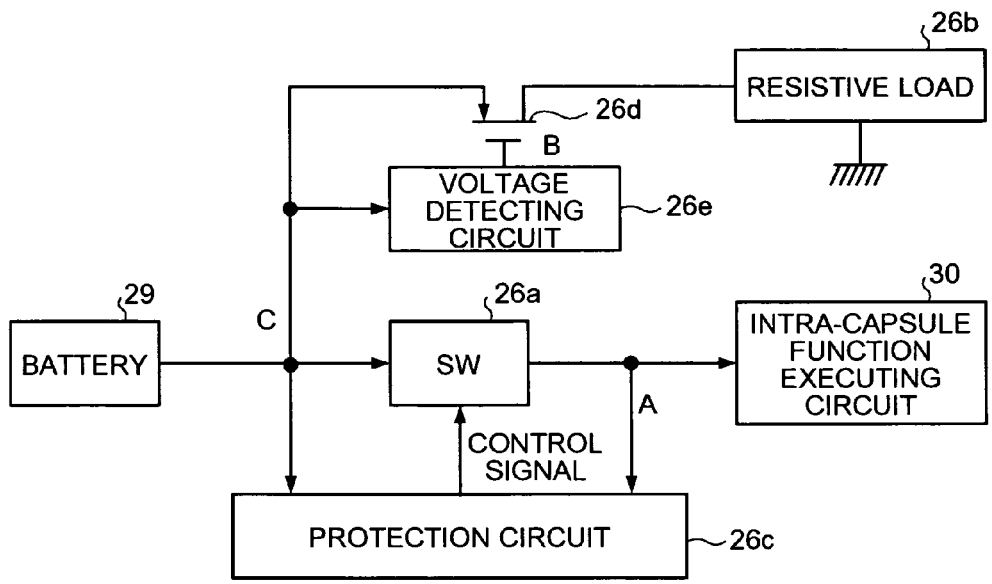
FIG. 6 is a block diagram of a circuit configuration of a system control circuit shown in FIG. 2, according to a second embodiment of the present invention.

FIG. 6 is a block diagram for describing a circuit configuration of a system control circuit shown in FIG. 2, according to a second embodiment of the present invention. In FIG. 6, a difference from the first embodiment shown in FIG. 3 is that not only is the switch element 26a configured to enable to switch an ON/OFF state between the battery 29 and the intra-capsule function executing circuit 30, but a field effect transistor (FET) 26d that is capable of performing the switching of the ON/OFF state between the battery 29 and the resistive load 26b, and a voltage detecting circuit 26e that performs the switching control of the FET 26d by detecting the voltage value at the point C separately from the protection circuit 26c are included.

Figure 7:
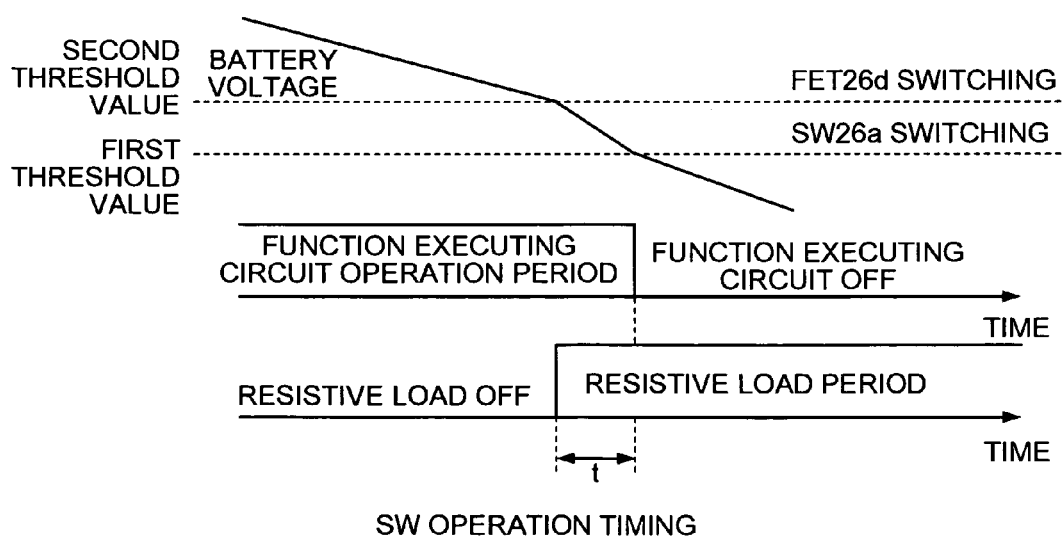
FIG. 7 a schematic view for describing a threshold value set in a protection circuit and in a voltage detecting circuit shown in FIG. 6 and a switching timing of a switch element and a field effect transistor (FET) based on the threshold value.

In the protection circuit 26c, as shown in FIG. 7, a first threshold value set as the substantially same threshold value in the first embodiment is set. When the voltage value at the point A becomes smaller than the first threshold value, the protection circuit 26c determines that the intra-capsule function executing circuit 30 becomes in difficulty to perform a normal operation, and terminates the electric power supply to the intra-capsule function executing circuit 30 by performing the switching control of the switch element 26a to be in the OFF state.

In the FET 26d, a source terminal is connected to the battery 29, a drain terminal is connected to the resistive load 26b, and a gate terminal is connected to the voltage detecting circuit 26e. Further, in the voltage detecting circuit 26e, as shown in FIG. 7, a second threshold value that is a higher voltage value than the first threshold value is set. The second threshold value is set in advance as a value with which, for example, if the voltage value at the point C becomes smaller and the driving power is exhausted by the resistive load 26b, the normal operation of the intra-capsule function executing circuit 30 is not affected. In other words, according to the present embodiment, a period "t" is provided during which the electric power is supplied both to the intra-capsule function executing circuit 30 and to the resistive load 26b. Due to the electric power supply to the both loads, the exhaustion of the electric power stored in the battery 29 can be accelerated. According to the present embodiment, it is acceptable to configure the switch element 26a by the above described FET.

The operation of the capsule endoscope 2 according to the second embodiment is described with reference to a block diagram shown in FIG. 6. In FIG. 6, similar to the first embodiment, the driving energy is supplied from the battery 29 to the intra-capsule function executing circuit 30 by removing the capsule endoscope 2 from the package. The voltage detecting circuit 26e detects the voltage at the point C, and when the voltage value is not smaller than the second threshold value, the electric power is exclusively supplied to the intra-capsule function executing circuit 30.

Thereafter, due to the electric power supply to the intra-capsule function executing circuit 30, the battery power is exhausted. When the voltage at the point C becomes smaller than the second threshold value, an output is generated from the voltage detecting circuit 26e to the gate terminal of the FET 26d, a current is flown between the source and the drain terminals of the FET 26d due to the output, and the electric power from the battery 29 is supplied to the resistive load 26b. At this state, the electric power is supplied both to the intra-capsule function executing circuit 30 and to the resistive load 26b, and the exhaustion of the battery power is accelerated as shown in FIG. 7.

In this situation, the battery power is more and more exhausted, and when the voltage at the point A becomes smaller than the set threshold value, the protection circuit 26c detects the situation, determines that the intra-capsule function executing circuit 30 becomes in difficulty to perform the normal operation, switches the switch element 26a to be in the OFF state, and terminates the electric power supply to the intra-capsule function executing circuit 30. Accordingly, the battery power is exclusively supplied to the resistive load 26b and can be exhausted with the inclination characteristic shown in FIG. 7.

As described, according to the present embodiment, when the battery voltage becomes smaller than the predetermined second threshold value, the FET is changed to be in the ON state, and the electric power is supplied to the intra-capsule function executing circuit and to the resistive load to accelerate the power consumption. Further, when the battery voltage becomes smaller than the first threshold value, the switch element is switched to be in the OFF state, the electric power supply to the intra-capsule function executing circuit is terminated, and electric power stored in the battery is exhausted by the resistive load. As a result, the electric power stored in the battery in the body insertable apparatus can rapidly be exhausted, and a false operation of the circuit at the midpoint potential can easily be prevented.

Figure 8:
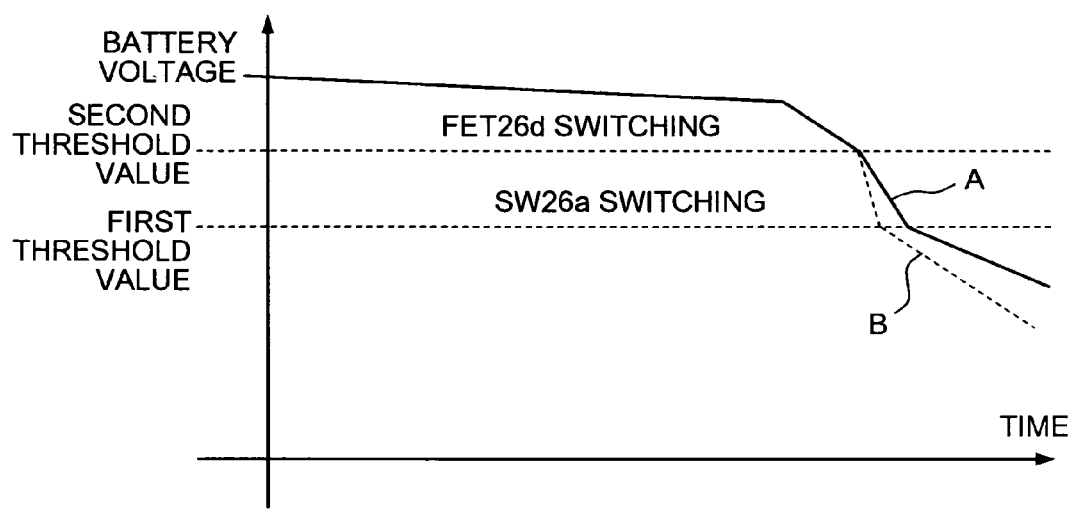
FIG. 8 is a schematic view for describing a variation of a battery voltage when a resistance value of a resistive load shown in FIG. 6 is changed.

Further, according to the present embodiment, by changing a resistance value of the resistive load, for example, from R1 to R2 (R2<R1), as shown in a schematic view for describing a variation of the battery voltage in FIG. 8, the battery voltage is shifted from a change shown with a solid line A to a change shown with a dashed line B. As a result, the electric power stored in the battery in the body insertable apparatus can rapidly be exhausted in a short time.

INDUSTRIAL APPLICABILITY

As described above, the body insertable apparatus according to the present invention is suitable for a medical observation apparatus to be inserted into a human body for observing an examined region, and specifically suitable for preventing a false operation of a circuit at a midpoint potential by exhausting electric power stored in a battery in the body insertable apparatus.

The invention claimed is:

1. A body insertable apparatus comprising:
   a function executing unit that executes a predetermined function in a body into which the body insertable apparatus is inserted;
   an electric-power accumulating unit that accumulates driving power for driving the function executing unit;
   a detector that detects electric power supplied from the electric-power accumulating unit;
   an exhaustion unit that is provided separately from the function executing unit and exhausts the electric power in the electric-power accumulating unit; and
   a switching controller that switches electric power supply from the electric-power accumulating unit, from the function executing unit to the exhaustion unit, based on a detection result of the detector;
   wherein the switching controller supplies electric power from the electric-power accumulating unit to the function executing unit and to the exhaustion unit at the same time, and subsequently performs a switching for making the electric power supply to the function executing unit terminatably, based on the detection result of the detector.

2. The body insertable apparatus according to claim 1, wherein the function executing unit comprises:
   an illuminating unit that illuminates an inside of the body;
   an acquiring unit that acquires image information on the illuminated inside of the body; and
   a radio transmitting unit that wirelessly transmits the image information on the inside of the body acquired by the acquiring unit to an outside, and
   the switching controller switches the electric power supply from the electric-power accumulating unit to the function executing unit and to the exhaustion unit, based on the detection result of the detector and a predetermined error rate of the image information.

3. A method of exhausting electric power in a body insertable apparatus comprising:
   executing a predetermined function by a function executing unit in a body into which the body insertable apparatus is inserted;
   accumulating driving power for driving the function executing unit by an electric-power accumulating unit;
   detecting an electric power supplied from the electric-power accumulating unit by a detector;
   switching an electric power supply from the electric-power accumulating unit, from the function executing unit to an exhaustion unit, based on a detection result of the detector; and
   exhausting the electric power in the electric-power accumulating unit by the exhaustion unit;
   wherein the switching of the electric power from the electric-power accumulating unit to the function executing unit and to the exhaustion unit is performed at the same time, and subsequently a switching of the electric power supply to the function executing unit is performed terminatably, based on the detection result of the detector.

4. The method of exhausting electric power in a body insertable apparatus according to claim 3, wherein the function executing unit comprises:
   an illuminating unit that illuminates an inside of the body;
   an acquiring unit that acquires image information on the illuminated inside of the body; and
   a radio transmitting unit that wirelessly transmits the image information on the inside of the body acquired by the acquiring unit to an outside, and
   the switching of the electric power supply from the electric-power accumulating unit to the function executing unit and to the exhaustion unit is performed based on the detection result of the detector and a predetermined error rate of the image information.

* * * * *